United States Patent [19]
Shirafuji et al.
[11] Patent Number: 4,691,064
[45] Date of Patent: Sep. 1, 1987

[54] METHOD FOR PRODUCING CYCLOALKANOLS

[75] Inventors: Tamio Shirafuji; Itaru Kawata, both of Niihama, Japan

[73] Assignee: Sumitomo Chemical Company, Limited, Osaka, Japan

[21] Appl. No.: 929,512

[22] Filed: Nov. 12, 1986

[30] Foreign Application Priority Data

Nov. 22, 1985 [JP] Japan ................................ 60-262853

[51] Int. Cl.$^{4}$ ...................... C07C 35/06; C07C 35/08; C07C 35/20

[52] U.S. Cl. .................................... 568/835; 568/821; 568/822; 568/838

[58] Field of Search ................ 568/821, 822, 835, 838

[56] References Cited

U.S. PATENT DOCUMENTS 4,306,101 12/1981 Slaugh et al. ....................... 568/835
4,528,409 7/1985 Mitsui et al. ........................ 568/835

FOREIGN PATENT DOCUMENTS 8104 3/1968 Japan .................................. 568/835
16125 7/1968 Japan .................................. 568/835

OTHER PUBLICATIONS

Chemical Abstracts, 72, 12209z (Abstract of Japanese Pat. Publn. No. 26656/1969).
Chemical Abstracts, 78, 5778m (Abstract of Japanese Pat. Publn. No. 45323/1972).

*Primary Examiner*—Werren B. Lone
*Attorney, Agent, or Firm*—Stevens, Davis, Miller & Mosher

[57] ABSTRACT

A method for producing cycloalkanols important as a material for caprolactam, adipic acid and the like, which comprises carrying out the catalytic hydration of a cycloalkene using as a catalyst an aromatic sulfonic acid having at least one hydroxyl or ether group and separating the resulting cycloalkanol from the reaction solution by extraction.

9 Claims, No Drawings

METHOD FOR PRODUCING CYCLOALKANOLS

The present invention relates to a method for producing cycloalkanols which are important as a material for caprolactam, adipic acid, etc., and more particularly, to a method of producing cycloalkanols by the catalytic hydration of cycloalkenes.

For producing cycloalkanols by the hydration of cycloalkenes, methods with various catalysts are known.

Methods with mineral acids, particularly sulfuric acid are popularly known. Methods with a heteropoly-acid such as phosphotungstic acid, phosphomolybdic acid, etc. are disclosed in Japanese Pat. Publication No. 1089/1983.

Japanese Pat. Publication Nos. 8104/1968 and 16125/1968 disclose a method with aromatic sulfonic acids as a catalyst. Further, the following various methods are known: A method with mineral acids supported on carriers as a solid catalyst; a method with cation exchange resins (Japanese Pat. Publication Nos. 15619/1963 and 26656/1969); and a method with zeolite (Japanese Pat. Publication No. 45323/1972).

In the method with a solid catalyst, the life of the catalyst becomes a problem, the catalyst failing to maintain stable activity over a long period of time.

In the method with a soluble acid catalyst, the separation of the products, etc. is troublesome, requiring large quantities of energy.

In the method including esterification with a high-concentration sulfuric acid and hydrolysis, the recovery of sulfuric acid and removal of by-products are difficult. For the aromatic sulfonic acid, p-toluenesulfonic acid, benzenesulfonic acid, naphthalenesulfonic acid, etc. are used. When these acids are used as catalyst, most of cycloalkanol produced is present after reaction in the aqueous phase containing the catalyst, and therefore, when the cycloalkanol is separated from said reaction solution by extraction, the extraction efficiency is poor and large amounts of extraction solvent are necessary. This method, therefore, may not always be said to be desirable.

If separation of the cycloalkanol is carried out by distillation, the cycloalkanol and water form an azeotropic mixture, and besides, in the case of cyclohexanol, the weight ratio of cyclohexanol to water of the azeotropic mixture is as low as less than 0.2, so that large quantities of energy are required.

An object of the present invention is to find a method of producing cycloalkanols by the hydration of cycloalkenes which enables said cycloalkanols to be obtained in high yields and yet with little energy.

The present inventors extensively studied to solve these problems, and as a result, found that, by using aromatic sulfonic acids having a hydroxyl or ether group as a catalyst, extraction operation for the reaction solution can be carried out with a markedly improved percent extraction. The present inventors thus completed the present invention.

The present invention provides a method for producing cycloalkanols characterized in that the catalytic hydration of a cycloalkene is carried out using an aromatic sulfonic acid having at least one hydroxyl or ether group as a catalyst, and the formed cycloalkanol is separated from the reaction solution by extraction.

According to the present invention, by using aromatic sulfonic acids having at least one hydroxyl or ether group as a catalyst, almost the same reactivity as in the case wherein p-toluenesulfonic acid is used as the aromatic sulfonic acid is obtained, and besides, extraction operation for the reaction solution after reaction can be carried out with higher extraction efficiency and therefore with less extraction solvent than in the use of p-toluenesulfonic acid. Cycloalkanols can therefore be separated at low costs.

In the method of the present invention, the cycloalkene used as a material are preferably these having from 5 to 8 carbon atoms. For example, there may be mentioned cyclopentene, cyclohexene, cyclooctene, 1,5-cyclooctadiene, etc.

The catalyst used in the present invention includes for example monosulfonic acids and polysulfonic acids such as p-phenolsulfonic acid, hydroquinonesulfonic acid, 3,4-dihydroxybenzenesulfonic acid, pyrogallolsulfonic acid, cresolsulfonic acid, sulfosalicylic acid, naphtholsulfonic acid, methoxybenzenesulfonic acid, methoxysulfobenzoic acid, diphenylethersulfonic acid, 3-chloro-4-hydroxybenzenesulfonic acid, etc.

As to the catalyst concentration in the present invention, with an increase in the catalyst concentration of the aqueous solution, the yield of cycloalkanol increases, but extraction of cycloalkanol becomes difficult. Consequently, the catalyst is used as aqueous solution of, generally, from about 10 to about 80 wt. %, preferably from 30 to 70 wt. % in concentration.

In the present invention, the amount of the catalyst used depends largely upon the form of reaction, so that it cannot be determined unconditionally. Generally, however, amounts in a range of from about 0.1 to about 100 parts by weight based on 1 part by weight of cycloalkene are preferred. When the amount of catalyst is less than 0.1 part by weight, the reaction rate is low, while if amounts more than 100 parts by weight are used, the effect corresponding thereto cannot be obtained.

The amount of water used in the method of the present invention is generally about 1 to about 100 moles based on 1 mole of the cycloalkene.

In the present invention, the reaction temperature is in a range of from about 30° C. to about 200° C., particularly preferably in a range of from 70° to 150° C.

The reaction can be carried out either at atmospheric pressure or under pressure, and also it can be carried out by either batchwise form or continuous form.

For carrying out extraction, the reaction solution is separated into an oily and aqueous phases, and the aqueous phase, as such or after diluted with water is brought into contact with an extraction solvent to extraction-separate a cycloalkanol.

The solvent used for separation may be any of cycloalkenes used in reaction and solvents inert to the reaction of the present invention. Preferably, aromatic hydrocarbons such as benzene, toluene, xylene, etc. are used.

The present invention will be illustrated specifically with reference to the following examples, but it is not limited to these examples.

The percent extraction of cycloalkanol shown in the examples is given by the equation:

Percent extraction (%) =

-continued $$\frac{\text{Weight of cycloalkanol in extraction solvent}}{\text{Weight of total cycloalkanol}} \times 100$$

EXAMPLE 1

To a 1-liter autoclave, made of pressure-proof glass, were added 150 g of cyclohexene, 270 g of water and 270 g of sulfosalicylic acid, and after replacing air in the autoclave by nitrogen, reaction was carried out at 120° C. for 2 hours.

After completion of the reaction, the reaction solution was analyzed by gas chromatography to find that the conversion of cyclohexene was 37% and the selectivity of cycloalkanol was 97%.

The reaction solution was then separated into an oily and aqueous phases. 580 Grams of the resulting aqueous phase was added to a 2-liter three-necked flask, and after adding the same weight of benzene (580 g) thereto, the mixed solution was stirred at 70° C. for 1 hour. After allowing the solution to stand still for several minutes, the solution was separated into an oily and aqueous phases, and cyclohexanol contents were analyzed. The composition of the aqueous phase after reaction and the compositions of the aqueous and oily phases after extraction are shown in Table 1.

TABLE 1

| | Composition (g) | | | | |
|---|---|---|---|---|---|
| | cyclo-hexanol | Cyclo-hexene | Water | Sulf-salicylic acid | Benzene |
| Aqueous phase after reaction | 44 | 1 | 267 | 268 | 0 |
| Aqueous phase after extraction | 16 | 0 | 265 | 265 | 0 |
| Oily phase after extraction | 28 | 1 | 2 | 3 | 580 |

As can be seen from the table, the percent extraction of cyclohexanol was 64%.

EXAMPLES 2 to 7

Hydration and extraction were carried out in the same manner as in Example 1 except that sulfosalicyclic acid was replaced by each of p-phenolsulfonic acid, hydroquinonesulfonic acid, cresolsulfonic acid, methoxybenzene-sulfonic acid, naphtholsulfonic acid and 3-chloro-4-hydroxybenzenesulsonic acid.

The results of reaction and percent extraction of cyclohexanol are shown in Table 2.

TABLE 2

| Example | Catalyst | Conversion of cyclohexene (%) | Selectivity of cyclohexanol (%) | Percent extraction of cyclohexanol (%) |
|---|---|---|---|---|
| 2 | p-Phenolsulfonic acid | 33 | 95 | 73 |
| 3 | Hydroquinonesulfonic acid | 28 | 98 | 81 |
| 4 | Cresolsulfonic acid | 33 | 95 | 78 |
| 5 | Methoxybenzenesulfonic acid | 27 | 99 | 68 |
| 6 | Naphtholsulfonic acid | 25 | 99 | 83 |
| 7 | 3-Chloro-4-hydroxy-benzenesulfonic acid | 25 | 96 | 73 |

Comparative Examples 1 to 3

Hydration and extraction were carried out in the same manner as in Example 1 except that sulfosalicylic acid was replaced by each of p-toluenesulfonic acid, benzenesulfonic acid and naphthalenesulfonic acid.

The results of reaction and percent extraction cf cyclohexanol are shown in Table 3.

TABLE 3

| Comparative Example | Catalyst | Conversion of cyclohexene (%) | Selectivity of cyclohexanol (%) | Percent extraction of cyclohexanol (%) |
|---|---|---|---|---|
| 1 | p-Toluenesulfonic acid | 31 | 93 | 38 |
| 2 | Benzenesulfonic acid | 27 | 95 | 37 |
| 3 | Naphthalenesulfonic acid | 31 | 94 | 21 |

According to the present invention, in practicing a method of producing cycloalkanols by the hydration of cycloalkenes, by using aromatic sulfonic acids having at least one hydroxyl or ether group as a catalyst, almost the same reactivity as in the conventional methods is obtained, and besides, the percent extraction of cycloalkanol from the reaction solution is greatly improved.

What is claimed is:

1. A method for producing cycloalkanols which comprises carrying out the catalytic hydration of a cycloalkene having from 5 to 8 carbon atoms with water using as a catalyst an aromatic sulfonic acid having at least one hydroxyl or ether group at a temperature in the range from about 30° C. to about 200° C., and separating the resulting cycloalkanol from the reaction solution by extraction.

2. A method according to claim 1, wherein the cycloalkene having from 5 to 8 carbon atoms is cyclopentene, cyclohexene, cyclooctene or 1,5-cyclooctadiene.

3. A method according to claim 1, wherein the cycloalkene and the cycloalkanol corresponding thereto are cyclohexene and cyclohexanol, respectively.

4. A method according to claim 1, wherein the aromatic sulfonic acid used as the catalyst is one member selected from the group consisting of p-phenolsulfonic acid, hydroquinonesulfonic acid, 3,4-dihydroxybenzenesulfonic acid, pyrogallolsulfonic acid, cresolsulfonic acid, sulfosalicyclic acid, naphtholsulfonic acid, methoxybenzenesulfonic acid, methoxysulfobenzoic acid, diphenylethersulfonic acid and 3-chloro-4-hydroxybenzenesulfonic acid.

5. A method according to claim 1, wherein the catalyst concentration is from about 10 to about 80 wt. %.

6. A method according to claim 1, wherein the amount of the catalyst used is from about 0.1 to about 100 parts by weight based on 1 part by weight of the cycloalkene.

7. A method according to claim 1, wherein the amount of the water used is from about 1 to about 100 moles based on 1 mole of the cycloalkene.

8. A method according to claim 1, wherein the solvent used for extraction of the cycloalkanol is aromatic hydrocarbon or cycloalkene used in reaction.

9. A method according to claim 1, wherein aromatic hydrocarbons is benzene, toluene, or xylene, or a mixture thereof.

* * * * *